United States Patent [19]

Chang et al.

[11] Patent Number: 4,910,139
[45] Date of Patent: Mar. 20, 1990

[54] METHOD FOR CONTINUOUSLY PRODUCING CITRIC ACID BY DUAL HOLLOW FIBER MEMBRANE BIOREACTOR

[75] Inventors: Ho Nam Chang; Bong Hyun Chung, both of Seoul, Rep. of Korea

[73] Assignee: Korea Advanced Institute of Science and Technology, Seoul, Rep. of Korea

[21] Appl. No.: 226,718

[22] Filed: Aug. 1, 1988

[30] Foreign Application Priority Data

Sep. 9, 1987 [KR] Rep. of Korea ............... 1987-9944

[51] Int. Cl.$^4$ .................... C12P 7/48; C12R 1/645
[52] U.S. Cl. ...................... 435/144; 435/917
[58] Field of Search ................ 435/144, 917

[56] References Cited

FOREIGN PATENT DOCUMENTS 2507500 12/1982 France ..................... 435/144
0907072 2/1982 U.S.S.R. .................. 435/144

OTHER PUBLICATIONS

Derwent Abstract, 82-64080E/31, Eysmond Fr 2496122, (6-82).
Biotech, 88-0857, Chung et al., Biotech Bioeng, 1988, 32, 2, 205-12.
Biotech, 87-08034, Eikmeier Z. Naturforsch C, (1987), 42, 4, 408-13.
Biotech, 87-01837, Chang et al., ACS Symp., (1986), 314.
Biotech, 85-02469, Mahala et al., World Biotech Rep., 1984, 2, A129-140.
Derwent Abs., 79-45384 B/24, Metkin et al., SU-619511, (7-1978).
Derwent Abs., 78-71922A/40, Metkin et al., SU 579303, (11-1978).
Derwent Abs., 81-00326D/01, Blain et al., GB 1581832, (12-1980).

*Primary Examiner*—Herbert J. Lilling
*Attorney, Agent, or Firm*—Townsend & Townsend

[57] ABSTRACT

*Aspergillus niger* B60 was immobilized in a dual hollow fiber bioreactor to produce citric acid continuously. The fungi proliferated well in the interstitial region formed by a parallel arrangement of three microporous polypropylene hollow fibers contained within a silicone tube. Excessive fungal cell growth could be controlled by supplying a nitrogen-deficient medium at the production stage, and also uniform cell distribution in the reactor could be obtained by changing the direction of medium flow. With pure oxygen aeration and nitrogen-deficient medium, volumetric productivity reached 1.62 g/l.h at a residence time of 4.02 h, which corresponded to a 27-fold increase over that of shake-flask fermentation. When the residence time was increased to 20.1 h, citric acid at a concentration of 26 g/l was continuously produced, with a yield of 80-90% and a volumetric productivity of 1.3 g/l.h. This represents a significant improvement in final concentration, yield and the volumetric productivity over the equivalent values of the corresponding batch formentation, which were 18 g/l, 40% and 0.06 g/l.h, respectively.

2 Claims, 2 Drawing Sheets

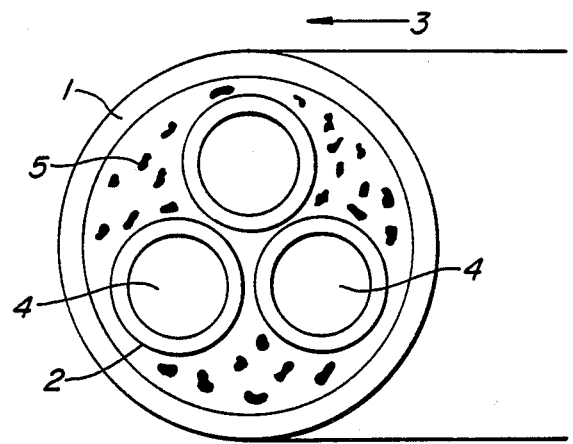
FIG._1.
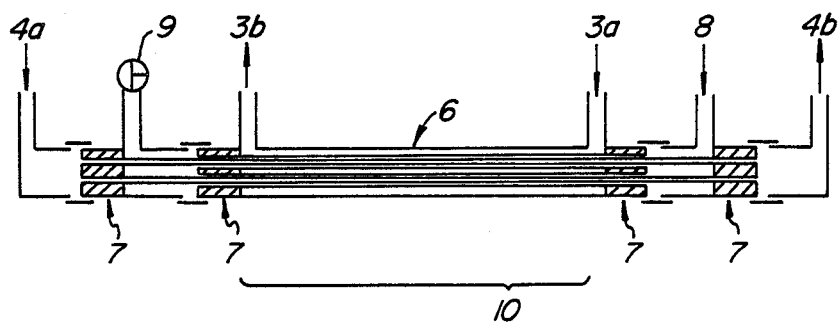
FIG._2.

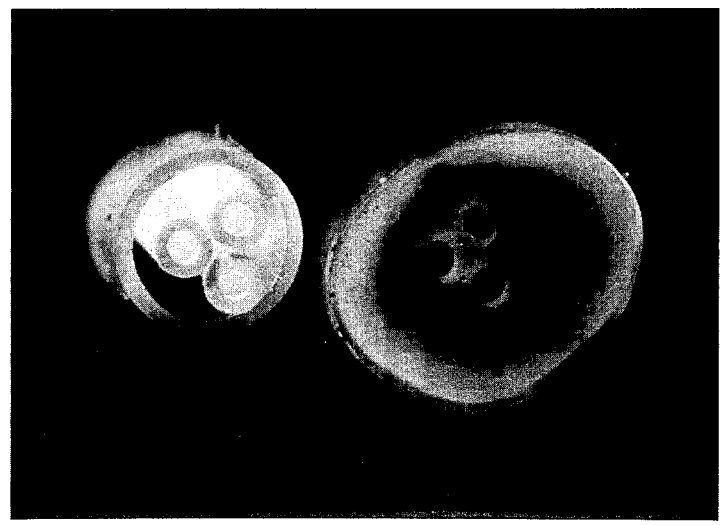
FIG._3.

METHOD FOR CONTINUOUSLY PRODUCING CITRIC ACID BY DUAL HOLLOW FIBER MEMBRANE BIOREACTOR

BACKGROUND OF THE INVENTION

1. Field of the Invention

The present invention relates to the method for producing citric acid on a continuous basis, after fixing Aspergillus niger B60 as mildews, in a dual hollow fiber membrane bioreactor.

2. Description of the Related Art

Recently, citric acid is commonly produced by fermentation, 20 percent of them is produced by surface culture and remaining 80 percent by submerged culture (Sodeck et al., Proc. Biochem. Oct./Nov., 9, 1981). However, such methods according to the prior art are batch operation which have a disadvantage of lower productivity in comparison with continuous operation according to present invention. As the existing continuous methods improved on the batch method, there are (1) a method utilizing a fermenter equipped with an agitator (Kristiansen and Sinclair, Biotechnol. Bioeng., 21, 297, 1979), (2) a method utilizing air-lift reactor after fixing *Aspergillus niger* mycelium to alginate bead (Vaija et al., Appl. Biochem. Biotechnol., 7, 51, 1982) and (3) a method utilizing tower reactor after the fixation of *Aspergillus niger* to polyacrylamide (Horitsu et al., Appl. Microbiol. Biotechnol., 22, 8, 1985).

The continuous operations in the existing method (1)~(3) brought higher productivity, but less concentration than the batch operation as in the case of other continuous operations, and required higher costs for the process of purification.

Moreover, when carriers are used to fix mildews, there was a tendency to weaken the carriers due to an excessive growth of cells. Leaving the carriers, cells, also, grow in liquid culture medium to cause many operational difficulties in the case of continuous operation.

SUMMARY OF THE INVENTION

The method according to the present invention has overcome the above described difficulties by utilizing dual hollowfiber membrane bioreactor, and obtained higher citric acid concentrations than the batch operation as well as higher productivity. In accordance with the present invention, cells are separated from the product by a membrane between them so that eliminate primary purification process which is essential in the ordinary fermentation process. Therefore, the present invention has processwise advantage saving considerable amount of energy required for aeration and agitation in the case of ordinary fermentation.

A dual hollow fiber membrane type biological bioreactor had been made by modifying the existing hollowfiber membrane bioreactor for the culture of aerobic bacteria. Robertson and Kim inserted three silicone tubes into a polypropylene hollowfiber membrane to supply liquid nutrients outside the polypropylene membrane, while oxygen into silicon tubes. Culturing Aerobic *Streptomyces aureofaciens* bacteria between them they carried out the researches related to continuous production of tetracycline (Robertson and Kim, Biotechnol. Bioeng., 27, 1012, 1985).

After then, the inventors of the present invention have achieved successfully continuous production of rifamycin B at a first time by utilizing the bioreactor, unlike the bioreactor used by Robertson and Kim, which comprises a silicone tube for supplying oxygen to its outside, and three polypropylene hollow fiber membranes inserted into the silicone tube for feeding liquid nutrients, and *Nocardia mediterranei* is cultured between the tubes (Chan et al., ACS Symp. Ser. 314, 32, 1986).

The present invention is related to a method of producing citric acid on a continuous basis by utilizing the bioreactor developed by the present inventors and the details of the method will be described hereinafter with reference to the accompanying drawings.

BRIEF DESCRIPTION OF THE DRAWINGS

FIG. 1 is a sectional view of a dual hollow fiber membrane bioreactor;

FIG. 2 is a transverse sectional view of a double fine-tube reactor used in the present invention; and FIG. 3 is a three-dimensional microphotograph of the cross section of a dual hollow fiber membrane bioreactor and after the culture of cells.

DESCRIPTION OF THE PREFERRED EMBODIMENTS

FIG. 1 is a sectional view of a dual hollowfiber membrane of the bioreactor according to the present invention. In the drawing, three polypropylene hollowfiber membranes (2) are inside a silicone tube (1), while *Aspergillus niger* B60 (5) is contained in the space between the silicon tube (1) and three polypropylene hollowfiber membrane (2).

FIG. 2 is a transverse sectional view of the dual hollow fiber membrane bioreactor (10) which is used in the present invention. As shown in the drawing, the dual hollow fiber membranes of FIG. 1, where polypropylene tubes (2) are longer than the silicone tube (1), are laid in a glass tube (6) in parallel and then the ends of the silicone tube (1) and polypropylene fine tubes (2) are fixed with silicone rubber (7) respectively. At one end of the silicone tube (1), an oxygen supply inlet (3a) is provided while an air vent (3b) is provided at the other end. Between one end of the silicone tube (1) and polypropylene fine tubes (2) a three-way valve (9) is provided and a culture strain inlet (8) on the other side. One end of the glass tube is fitted with a liquid culture medium inlet (4a) while a culture medium and product citric acid outlet (4b) is fitted on the other side.

After inoculating bacteria in the space between the inside of the silicone tube (1) and the outside of polypropylene tubes (2) through a culture strain inlet (8), liquid culture medium (4) is fed in the direction of a liquid culture medium and citric acid discharge outlet (4b) through a liquid culture medium inlet (4a), while oxygen (3) is supplied in the direction of an air vent (3b) from an oxygen feed inlet (3a).

The concentration of cells in the bioreactor (10) is equalized by alternately changing the feeding direction of liquid culture medium by means of a three-way valve (9). After the growth of cells comes to an end, the liquid culture medium deficient in nitrogen source is supplied to ensure stable operation of the bioreactor and also higher productivity.

The polypropylene fine tubes used in the fabrication of the bioreactor in the present invention where Enka items of Germany, measuring 0.033 cm in inner diameter and 0.063 cm in outer diameter, with pore sizes ranging from 0.4 to 0.6 μm. The silicone tube was Dow Corning product of the United States, with its inner diameter is 0.147 cm and outer diameter 0.196 cm. Eight double fine tubes were laid in a glass tube of 0.8 cm inner diameter, and the length of their possible contact with oxygen was 16 cm.

However, the scope of the present invention is not limited to the bioreactor used herein. That is, materials other than silicone and polypropylene can be used in the fabrication of a bioreactor and its structure can be also diverse depending upon the specification of fine tubes to be used, the number of fine tubes to be inserted can be widely adjusted.

FIG. 3 is a three-dimensional microphotograph showing the cross section of a dual hollow fiber membrane before (left) and after (right) the culture of cells. As shown in the microphotograph, *Aspergillus niger* B60 is cultured in high concentration in the space between the silicone tube (1) and polypropylene hollow fiber membrane (2) by feeding oxygen and liquid culture medium.

In accordance with the present invention, it is possible to obtain excellent results which are higher by 40–50 percent in yield and 22–27 times in productivity than those in the batch operation in a conventional shaking incubator. It has an advantage of easy separation and purification since citric acid is produced continuously by fine tubes under separate state from cells.

Following examples are descriptions of the conventional method (comparative embodiment) and the present invention. But the present invention is not limited to these examples.

Comparative Example

*Aspergillus niger* B60 was inoculated to a 500-ml triangular flask containing 100 ml of liquid culture medium (Composition: sugar 6 g, $NH_4NO_3$ 0.25 g, $KH_2PO_4$ 0.1 g, $MgSO_4.7H_2O$ 0.025 g, pH 3.1) to be adjusted to an initial spore concentration of $10^7$–$10^8$ spores per 100 ml and then it was cultured in a shaking incubator at 300 rpm and 30° C.

After 10 days of incubation, the volume of citric acid was measured by the method of Marier and Boulet (Marier and Boulet, J. Dairy Sci., 41, 1683, 1958), while sugar concentration was determined by the method of Dobois and others for the total sugar concentration in culture medium (Dubois et al., Anal. Chem. 28, 350, 1956) on the basis of cane sugar and found that 18 g/liter of citric acid was produced, with its yield and productivity standing at 40 percent and 0.06 g/liter hour, respectively.

Example

The polypropylene fine tubes (2) of FIG. 2 were dipped in 50% ethanol and sterilized with 5% formalin and then sufficiently washed with sterilized distilled water, after then, *Aspergillus niger* B60 cultured in a shaking incubator for seven days was inoculated in the space between the silicone tube (1) and polypropylene fine tubes (2) through a culture strain inlet (8) as shown in FIG. 2. It was supplied with oxygen in the direction of an air vent (3b) from an oxygen inlet (3a) at 28°–30° C. for 10 days, while the liquid culture medium as used in the comparative example was fed in the direction of a citric acid discharge outlet (4b) from a liquid culture medium inlet (4a), to cultivate the cells in high concentration. The feeding direction of liquid culture medium was alternately changed by means of three way valve to equalize the concentration of cells in the bioreactor.

Further, the product was collected from a citric acid outlet (4b), while continuously feeding the culture medium deficient in $NH_4NO_3$ and the collected citric acid was measured. The product was 6.5 g/liter at the flow rate of 2 ml/hour. Its productivity was 1.62 g/liter hour, and 27 times of the comparative example.

After 15 days, the flow rate was changed to 0.9 ml/h, and the product was 13.5 g/liter. Its yield and productivity were 80–90 percent and 1.5 g/liter hour respectively. Changing the flow rate to 0.4 ml/h after 24 days, 26 g/liter of citric acid was produced while its yield and productivity registered 80–90 percent and 1.3 g/liter hour, respectively, and 22 times of the comparative example.

What is claimed is:

1. A method for continuously producing citric acid utilizing a dual hollow fiber membrane bioreactor comprising the steps:
    inoculating *Aspergillus niger* B60 in the space between hollow fibers and outer tube of said bioreactor,
    culturing said *Aspergillus niger* B60 in high concentration by feeding liquid culture medium into said hollow fibers supplying oxygen outside of said outer tube, and then,
    feeding said liquid culture medium which contains no $NH_4NO_3$ into said hollow fiber membrane, supplying oxygen outside of said outer tube.

2. A method according to claim 1, the feeding direction of said liquid culture medium being changeable alternately by means of a three way valve to equalize the high concentration of *Aspergillus niger* B60 to be cultured in the bioreactor.

* * * * *